United States Patent [19]
Qian

[11] Patent Number: 5,859,089
[45] Date of Patent: Jan. 12, 1999

[54] DENTAL RESTORATIVE COMPOSITIONS

[75] Inventor: Xuejun Qian, Foothill Ranch, Calif.

[73] Assignee: The Kerr Corporation, Orange, Calif.

[21] Appl. No.: 886,681

[22] Filed: Jul. 1, 1997

[51] Int. Cl.⁶ .............................. C09J 5/02; C08K 3/34; A61K 6/08
[52] U.S. Cl. .................. 523/116; 524/549; 524/558; 524/559; 526/318.1; 433/228.1
[58] Field of Search .............................. 523/116; 524/549, 524/558, 559; 526/318.1; 433/228.1

[56] References Cited

U.S. PATENT DOCUMENTS

| | | | |
|---|---|---|---|
| 3,629,187 | 12/1971 | Waller | 260/41 |
| 3,814,717 | 6/1974 | Wilson et al. | 260/29.6 |
| 3,826,778 | 7/1974 | Dietz | 260/42.47 |
| 3,971,754 | 7/1976 | Jurecic | 260/42.15 |
| 4,143,018 | 3/1979 | Crisp et al. | 260/29.6 |
| 4,376,835 | 3/1983 | Schmitt et al. | 523/116 |
| 4,500,657 | 2/1985 | Kumar | 523/116 |
| 4,588,756 | 5/1986 | Bowen | 523/116 |
| 4,738,722 | 4/1988 | Ibsen et al. | 106/35 |
| 4,758,612 | 7/1988 | Wilson et al. | 524/6 |
| 4,861,808 | 8/1989 | Billington et al. | 523/116 |
| 4,872,936 | 10/1989 | Engelbrecht | 156/307.3 |
| 4,900,697 | 2/1990 | Akahane et al. | 501/57 |
| 5,063,257 | 11/1991 | Akahane et al. | 523/116 |
| 5,130,347 | 7/1992 | Mitra | 522/149 |
| 5,151,453 | 9/1992 | Ibsen et al. | 523/115 |
| 5,154,762 | 10/1992 | Mitra et al. | 106/35 |
| 5,218,070 | 6/1993 | Blackwell | 526/318 |
| 5,270,351 | 12/1993 | Bowen | 523/116 |
| 5,338,773 | 8/1994 | Lu et al. | 523/118 |

FOREIGN PATENT DOCUMENTS

| | | | |
|---|---|---|---|
| 1507981 | 4/1978 | United Kingdom | 523/116 |
| WO 95/22956 | 8/1995 | WIPO | A61K 6/083 |

*Primary Examiner*—Andrew E. C. Merriam
*Attorney, Agent, or Firm*—Wood, Herron & Evans, L.L.P.

[57] ABSTRACT

Dental restorative compositions of the composite resin/glass ionomer hybrid type and resins used in the compositions. The compositions contain an aromatic-moiety-containing polymerizable resin, a finely divided ion-leachable fluoroaluminosilicate glass filler, a polymerization initiator system, and may contain other components. The aromatic-moiety-containing polymerizable resin has at least one carboxylic acid group and at least one ethylenically unsaturated group such as a (meth)acrylate group. The compositions have improved mechanical strength, improved wear resistance, and sustained long-term fluoride release.

36 Claims, No Drawings

DENTAL RESTORATIVE COMPOSITIONS

FIELD OF THE INVENTION

The invention relates to dental restorative compositions of a composite resin/glass ionomer hybrid type and resins used in the compositions.

BACKGROUND OF THE INVENTION

Dental restoratives are materials that restore both the appearance and function of a defective tooth structure. Features desirable in a dental restorative are good coloring to match teeth, high polishability, limited or no shrinkage upon curing, good mechanical properties, sustained fluoride release, radiopacity, excellent bonding with the natural tooth structure, and a wear resistance similar to enamel. Examples of dental restoratives are glass ionomer restoratives, composite resin restoratives, and composite resin/glass ionomer hybrid type restoratives.

Glass ionomer restoratives were introduced to dentistry as dental luting cements and restorative materials about two decades ago. The material is packaged as a liquid/powder two-part system that must be mixed immediately prior to application. Hardening of a glass ionomer restorative is achieved through the reaction of a poly(carboxylic acid) with an ion-leachable fluoroaluminosilicate glass in the presence of water, forming a crosslinked network structure. Water is an essential ingredient needed for the setting reaction of a glass ionomer material.

Glass ionomer restoratives have the desirable properties of good adhesion to unconditioned dentin, cariostatic effect due to long-term fluoride release, and excellent biocompatibility. However, some undesirable properties that have limited their acceptance are their poor handling properties, lack of a command cure, moisture sensitivity during the early stage of the setting reaction, poor mechanical properties, and poor wear resistance. Glass ionomer restoratives find use in areas of the oral cavity where low stress is encountered as underfilling materials, luting cements, and in some cases as filling materials for gingival lesions.

Composite resin restoratives were created in parallel with glass ionomer restoratives. Composite resin restoratives appeared to solve all the problems associated with glass ionomer restoratives. Composite resin restoratives offer excellent aesthetics, easy handling, and much improved mechanical strength and wear resistance. However, composite resin restoratives alone do not release fluoride. Composite resin restoratives are comprised of (meth)acrylate resins, defined as resins containing either acrylate or methacrylate groups, reinforced with an inert inorganic filler. Hardening of the composite resin is achieved through free-radical polymerization of the (meth)acrylate monomers using a photoinitiator, a heat-cure initiator, or a redox initiator system.

Attempts have been made to combine glass ionomer and composite resin chemistries by introducing polymerizable (meth)acrylate monomers/oligomers/prepolymers and free-radical initiators into the glass ionomer system, leading to the development of a hybrid material. Two types of hybrid materials were created: a "resin-modified glass ionomer" (RMGI) type and a "compomer" type.

RMGI materials retain most of the characteristics of a conventional glass ionomer in that water is an essential ingredient, they are packaged as a liquid/powder two-part system that must be mixed prior to use, and there is a significant contribution from the ionic acid-base setting reaction. RMGI materials have improved the mechanical properties, and have eliminated the moisture sensitivity, of the conventional glass ionomer materials. However, their application is still limited to use in low stress bearing areas of the mouth due to their inadequate mechanical strength and wear resistance. Another problem is that RMGI restoratives, once placed in a restoration, tend to absorb excessive and uncontrolled amounts of water, causing crowns cemented with RMGI materials to fracture due to excessive hygroscopic expansion of the materials.

With RMGI materials, three curing mechanisms are possible: an acid-base setting reaction of the conventional glass ionomer type, photo-curing using photo-initiators, and chemical-curing using redox initiators via free-radical polymerization of the polymerizable vinyl groups.

The second type of hybrid material, called "compomers," are light-curable single-part paste systems. They contain the following key ingredients: a reactive fluoroaluminosilicate glass, (meth)acrylate monomers containing acid functional groups, and a curing initiator, usually a photoinitiator. They may also contain other copolymerizable (meth)acrylate monomers which do not contain acid functional groups. Water is absent from the composition; the material is in an anhydrous (non-aqueous) form.

The primary setting reaction of a compomer is free-radical photo-polymerization involving the vinyl functional groups. Compomers, as single-part resin-based materials, can only be hardened clinically through photo-curing. In this respect, compomers are clinically used in a way identical to light-curable composite resins. Light-curing of the (meth) acrylate monomers results in an inter-connected polymer network which is reinforced by enclosed reactive filler particles. This provides the immediate strength and resistance needed in the oral cavity. At this stage, existing acidic groups on the polymers remain inactive since the compomer is an anhydrous form which prevents the acid-base ionic reaction from occurring. Once placed into the moist environment of the mouth, however, the compomer begins to absorb water, thus completing the ingredients necessary to initiate an ionic acid-base reaction, i.e., acidic groups, a reactive filler, and water. This secondary ionic acid-base reaction serves to release fluoride, although it contributes little to the integrity and mechanical properties of the cured compomer. Besides long-term release of fluoride, another desirable characteristics of a compomer is its ability to absorb a small amount of water and, as a result, expand slightly to alleviate the shrinkage stress caused by the polymerization of the (meth)acrylate resin, thus contributing to good marginal integrity.

Compomers are composite resin/glass ionomer hybrid restoratives that combine, in one material, the desirable properties of glass ionomer restoratives and composite resin restoratives. Compomers have good aesthetics, easy handling, a command cure mechanism, good mechanical properties such as strength and wear resistance, long-term fluoride release, and a small amount of hygroscopic expansion. As a result, long-lasting restorations can be obtained with compomer materials, and their applications are being extended to areas in the oral cavity subject to moderate to high stresses. However, improvements in mechanical strength and wear resistance are still needed before compomers can truly replace composite resins as an anterior/posterior restorative material.

SUMMARY OF THE INVENTION

To this end, and in accordance with the principles of the present invention, a dental composite resin/glass ionomer hybrid restorative composition containing an aromatic-moiety-containing polymerizable resin, a finely divided ion-leachable fluoroaluminosilicate glass filler, and a polymerization initiator system is disclosed. Such resins and restorative compositions are improvements over the prior art.

The aromatic-moiety-containing polymerizable resin of the composition has at least one ethylenically unsaturated group and at least one carboxylic acid group. An especially preferred aromatic-moiety-containing polymerizable resin is the addition reaction product of a styrene-maleic anhydride oligomer (SM) or pyromellitic acid dianhydride (PM), and an organic compound having one reactive hydroxyl group and at least one ethylenically unsaturated group such as a (meth)acrylate group. Preferred organic compounds are 2-hydroxyethyl methacrylate (HEMA) or glyceroldimethacrylate (GDM). In one preferred embodiment, the aromatic-moiety-containing polymerizable resin is a (styrene-maleic anhydride oligomer)-(hydroxyethyl methacrylate) adduct (SM-HEMA) or a (styrene-maleic anhydride oligomer)-glyceroldimethacrylate adduct (SM-GDM). In preferred embodiments, the styrene-maleic anhydride oligomer has an average molecular weight in the range of about 300–3,000, most preferably in the range of about 1,000–3,000, and the (meth)acrylate pendant group is attached to the styrene-maleic anhydride oligomer backbone through an ester linkage. In another equally preferred embodiment, the aromatic-moiety-containing polymerizable resin is a (pyromellitic acid dianhydride)-(hydroxyethyl methacrylate) adduct (PMDM) or a (pyromellitic acid dianhydride)-glyceroldimethacrylate adduct (PMGDM). The meta-isomer of the PMDM reaction product is particularly preferred. The preferred concentration of the aromatic-moiety-containing polymerizable resin is in the range of about 0.1% by weight of the composition to about 90% by weight of the composition.

The fluoroaluminosilicate glass filler of the composition preferably has a concentration in the range of about 0.5% by weight to about 95% by weight, has a mean particle size of about 0.05 $\mu$m to about 20 $\mu$m, and is surface treated with a silane coupling agent.

The polymerization initiator system of the composition is preferably a photo-initiator system and the composition is a light-curable single-part composition. However, a redox chemical initiator system can also be incorporated into the composition, resulting in a two-part composition that is self-curable (chemical-cure) or dual-curable (photo-cure and chemical-cure).

The invention is also directed to the aromatic-moiety-containing polymerizable resins for use in a composite resin/glass ionomer hybrid dental restorative. These resins have at least one ethylenically unsaturated group and at least one carboxylic acid group. Preferably, a styrene-maleic anhydride oligomer or pyromellitic acid dianhydride reacts with either glyceroldimethacrylate or 2-hydroxyethyl methacrylate to form SM-GDM, SM-HEMA, PMDM, or PMGDM. When PMDM is the reaction product, the meta-isomer is preferably at least 20% of the reaction product.

The disclosed dental restoratives of the composite resin/glass ionomer hybrid type containing the disclosed resins provide the composition with improved physical properties, improved mechanical strength, improved wear resistance, and long-term fluoride release. Such resins and restorative compositions are improvements over the prior art. These and other objects and advantages of the present invention shall be made apparent from the following description and examples.

DETAILED DESCRIPTION

The dental restoratives of the present invention are of the composite resin/glass ionomer hybrid type. They are composed of an aromatic-moiety-containing polymerizable resin having at least one ethylenically unsaturated group and at least one carboxylic acid group, a finely divided ion-leachable fluoroaluminosilicate glass filler, and a polymerization initiator system. The compositions provide improved physical properties such as improved mechanical strength, improved wear resistance, and sustained fluoride release to a restorative.

The aromatic-moiety-containing polymerizable resin has at least one, and preferably at least two, carboxylic acid groups and at least one, and preferably at least two, ethylenically unsaturated groups. The carboxylic acid groups may be directly or indirectly attached to the aromatic structure. The preferred ethylenically unsaturated groups are (meth)acrylate groups, defined as containing either acrylate or methacrylate groups.

In one preferred embodiment, the aromatic-moiety-containing polymerizable resin is a monomer that is the addition reaction product between a pyromellitic acid dianhydride and an organic compound having one reactive hydroxyl group and at least one ethylenically unsaturated group. The organic compound preferably is glyceroldimethacrylate or 2-hydroxyethyl methacrylate. One most preferred aromatic-moiety-containing monomer is the addition reaction product of pyromellitic acid dianhydride and glyceroldimethacrylate to form a (pyromellitic acid dianhydride)- glyceroldimethacrylate adduct (PMGDM). The PMGDM reaction product is a mixture of meta- and para-isomers, with the meta-isomer shown as follows:

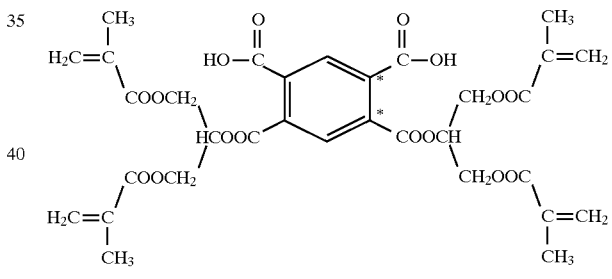

Another equally most preferred monomer is the addition reaction product of pyromellitic acid dianhydride and 2-hydroxyethyl methacrylate to form a (pyromellitic acid dianhydride)-(hydroxyethyl methacrylate) adduct (PMDM), as shown:

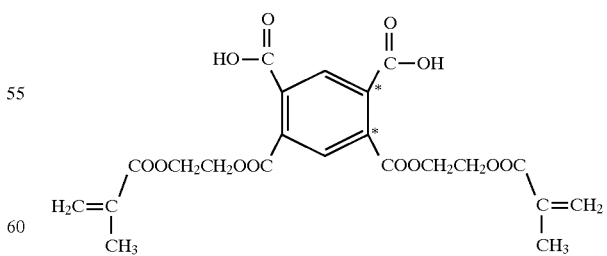

The PMDM reaction product is a mixture of meta- and para-isomers, with the meta-isomer more preferred than the para-isomer. In a particularly preferred embodiment, the reaction product after separation contains at least 20% of the meta-isomer.

In another equally preferred embodiment, the aromatic-moiety-containing polymerizable resin is an oligomer that is the addition reaction product between a styrene-maleic acid anhydride oligomer and an organic compound having one reactive hydroxyl group and at least one ethylenically unsaturated group. The organic compound preferably is glyceroldimethacrylate or 2-hydroxyethyl methacrylate.

One most preferred aromatic-moiety-containing oligomer is the addition reaction product of a styrene-maleic acid anhydride oligomer and 2-hydroxyethyl methacrylate to form a (styrene-maleic anhydride oligomer)-(hydroxyethyl methacrylate) adduct (SM-HEMA) as a reaction product, as shown:

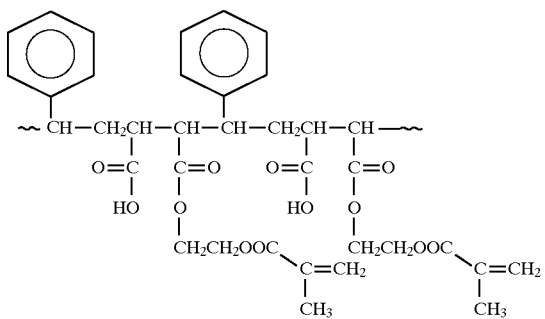

Another equally most preferred oligomer is the addition reaction product of glyceroldimethacrylate and styrene-maleic anhydride oligomer to form a (styrene-maleic anhydride oligomer)-glyceroldimethacrylate adduct (SM-GDM).

The above-described styrene-maleic anhydride oligomers have an average molecular weight in the range of about 300 to about 3,000, and preferably in the range of about 1,000 to about 3,000. The ethylenically unsaturated groups, such as (meth)acrylate groups, are preferably attached to the styrene-maleic anhydride oligomer backbone through an ester linkage.

The addition reactions are performed in an organic solvent in the presence of a catalyst. The catalyst may be a tertiary amine. The organic solvent may be a low-boiling point volatile organic compound which needs to be removed after the reaction is completed, or low viscosity monomers having at least one ethylenically unsaturated functional group. If the reaction is performed in a monomeric solvent, the reaction product can be directly formulated into the dental compositions of the present invention without removing the monomeric solvent. Some examples of suitable monomeric solvents are: 2-hydroxyethyl methacrylate, glyceroldimethacrylate, diethyleneglycol dimethacrylate, triethyleneglycol dimethacrylate, tetraethyleneglycol dimethacrylate, hexanediol dimethacrylate, trimethylolpropanetrimethacrylate, trimethylolpropanetriacrylate, and ethoxylated trimethylolpropanetriacrylate.

The concentration of the aromatic-moiety-containing monomers and/or oligomers is about 0.1–90% by weight of the composition, preferably about 1–60% by weight of the composition, and most preferably about 3–30% by weight of the composition.

The ion-leachable fluoroaluminosilicate glass filler of the composition is described in U.S. Pat. Nos. 4,143,018; 4,376,835; 4,738,722; and 4,900,697, which are hereby incorporated by reference in their entirety. In one embodiment, the fluoroaluminosilicate glass filler has a mean particle size in the range of about 0.05–20 $\mu$m. In preferred embodiments, the mean particle size is in the range of about 0.1–10 $\mu$m, and in most preferred embodiments, the mean particle size in the range of about 0.3–5 $\mu$m as measured by a sedimentation analyzer or a laser scattering method. The fluoroaluminosilicate glass filler is preferably surface-treated with a silane coupling agent such as γ-methacryloyloxypropyltrimethoxysilane (A-174 from Union Carbide Corp.). The fluoroaluminosilicate glass filler is about 0.5–95% by weight, preferably from about 5–90% by weight, and most preferably from about 40–80% by weight.

The preferred polymerization initiator system is a photoinitiator system. Such photoinitiator systems include benzoin, benzoin ethers and esters, 2,2-diethoxy acetophenone, and diketone compounds plus a reducing agent. The preferred photo-initiator systems include camphoroquinone plus ethyl 4-(N,N-dimethylamino) benzoate, 2-(ethylhexyl)-4-(N,N-dimethylamino) benzoate, and N,N-dimethylaminoethyl methacrylate. The composition may be a light-curable single-part composition. However, a redox chemical initiator system can also be incorporated into the composition, resulting in a two-part composition that is self-curable (chemical-cure) or dual-curable (photo-cure and chemical-cure). An example of a redox chemical initiator system is a peroxide-amine system.

The dental composite resin/glass ionomer hybrid restorative compositions may also include a polymerizable resin having at least one ethylenically unsaturated group. Preferred embodiments are those that have at least two ethylenically unsaturated groups, and the most preferred embodiments have at least two (meth)acrylate groups. Examples of polymerizable (meth)acrylate resins are hydroxyethyl methacrylate (HEMA), glyceroldimethacrylate (GDM), methacryloyloxyethyl maleate (MEMA), diethyleneglycol dimethacrylate (DEGDMA), triethyleneglycol dimethacrylate (TEGDMA), tetraethyleneglycol dimethacrylate, hexanediol dimethacrylate (HDMA), hexanediol diacrylate (HDDA), trimethylolpropanetrimethacrylate (TMPTMA), trimethylolpropanetriacrylate (TMPTA), ethoxylated trimethylolpropanetriacrylate (EOTMPTA), 2,2-bis[4-(2-hydroxy-3-methacryloylpropoxy)-phenyl]-propane (Bis-GMA), ethoxylated bisphenol A dimethacrylate (EBPADMA), and urethane dimethacrylate (UDMA, a reaction product of 2-hydroxyethyl methacrylate with 2,4,4-trimethylhexane diisocynate). The concentration range of the polymerizable monomers and/or oligomers is about 0–90% by weight.

The above compositions may also include one or more colloidal silicas with a concentration range of about 0–30% by weight for viscosity adjustment and improved handling characteristics. Examples of colloidal silicas are the "Aerosil" series OX-50, OX-130, and OX-200 silica sold by Degussa, and "Cab-O-Sil M5" and "Cab-O-Sil TS-530" silica sold by Cabot Corp. The colloidal silica is preferably surface treated with a silane coupling agent such as γ-methacryloyloxypropyltrimethoxysilane (A-174). The above compositions may also include a non-reactive filler that is a substantially non-ion-leachable filler, with a concentration range of about 0–75% by weight. Examples of non-reactive fillers include quartz and barium-, strontium-, zirconium-, zinc-, and aluminum-containing glasses. The non-reactive filler is in the form of finely divided particles with a mean particle size in the range of about 0.01–20 $\mu$m, preferably in the range of about 0.1–10 $\mu$m, and most preferably in the range of about 0.3–5 $\mu$m, as measured by a sedimentation analyzer or laser scattering method. The non-reactive filler is preferably surface-treated with a silane coupling agent such as γ-methacryloyloxypropyltrimethoxysilane (A-174).

A polymerization inhibitor such as 2,6-di-(tert-butyl)-4-methylphenol (BHT) and 4-methoxyphenol (MEHQ), may be added to prolong the shelf-life of the restorative mixtures. A UV stabilizer, such as 2-hydroxy-4-methoxybenzophenone (HMB) may also be added, and the above restorative compositions are mixed into a single-part light-curable paste.

The following technique was used to make compressive strength measurements on samples of the restorative compositions of the present invention, described in Examples 1–3 which follow. A stainless-steel split-mold with a mold dimension of 4 mm (diameter)×3 mm (height) was placed on a cellophane film. The mold was slightly overfilled with the sample paste, covered with another cellophane film, and then pressed between two glass plates to eliminate excess sample. The sample was photo-cured with a Demetron Optilux 401 curing light (Kerr Corp.) with a 30 second exposure on each side. The cured disk was removed from the mold and conditioned in 37° C. water for 24 hours before subjecting to mechanical testing on an Instron Universal Tester (Model 4202) in compression mode with a crosshead speed of 0.02"/minute. The peak load at which the specimen breaks is used to calculate the compressive strength, which is expressed in MPa unit.

The following technique was used to make fluoride release measurements on samples of the restorative composition of the present invention, described in Examples 1–3 which follow. A stainless-steel mold with a mold dimension of 20 mm (diameter)×1 mm (height) was placed on a 24 mm×50 mm glass coverslip. The mold was slightly overfilled with the sample paste and then covered with another glass coverslip. The mold and coverslips were pressed with a glass plate to eliminate excess sample. The sample was photo-cured with a Demetron Optilux 401 curing light (Kerr Corp.) with five 30 second exposures at five overlapping positions: center, 12 o'clock, 3 o'clock, 6 o'clock, and 9 o'clock. The cured disk was then polished on both surfaces on #240 grit wet SiC sandpaper and placed in 50 ml of 0.85 wt. % NaCl solution in a polyethylene screw cap vial. The samples were then stored in an oven kept at 37° C. and measured for fluoride release at 1 day, 1 week, 2 week, 3 week, and 4 week intervals, using an Orion® fluoride electrode and an Ion Analyzer (Orion Research Inc.). Prior to the measurement, the specimen disk was removed from the solution and 5 ml of TISAB III buffer solution was added to the sample solution. After measurement, the specimen disk was placed in a fresh NaCl solution and conditioned at 37° C. for measurements at a later time. The electrode was calibrated with known fluoride concentration standards (1 ppm and 10 ppm) just prior to measuring the sample solution. The cumulative fluoride release in $\mu$g of fluoride per $cm^2$ surface area of cured disk was then calculated and reported as a function of time.

In the following Examples 1–3 for making a paste, a homogeneous unfilled resin mixture was made first by mixing all resins with initiators and additives, and then the resin mixture was further blended together with appropriate fillers including colloidal silicas.

In Examples 1–3, the following materials were used:

A-174: γ-methacryloyloxypropyltrimethoxysilane
BHT: 2,6-di-(tert-butyl)-4-methylphenol
Bis-GMA: 2,2-bis[4-(2-hydroxy-3-methacryloylpropoxy)-phenyl]-propane
CQ: camphoroquinone
EOTMPTA: ethoxylated trimethylolpropanetriacrylate
EBPADMA: ethoxylated bisphenol A dimethacrylate
HEMA: 2-hydroxyethyl methacrylate
MEMA: methacryloyloxyethyl maleate
ODMAB: 2-(ethylhexyl)-4-(N,N-dimethylamino) benzoate
OX-50: fumed silica or colloidal silica sold by Degussa
PMGDM: the addition reaction product of pyromellitic acid dianhydride and glyceroldimethacrylate
SM-HEMA: the addition reaction product of styrene-maleic anhydride oligomer and HEMA
TEGDMA: triethyleneglycol dimethacrylate
TMPTMA: trimethylolpropanetrimethacrylate
TS-530: surface treated fumed silica or colloidal silica sold by Cabot Corp.
UDMA: reaction product of 2-hydroxyethyl methacrylate with 2,4,4-trimethylhexane diisocynate,
HMB: 2-hydroxy-4-methoxybenzophenone

EXAMPLE 1

A) Resin mixture composition

| Ingredients | Parts by weight |
|---|---|
| SM-HEMA* | 18.00 |
| UDMA | 18.00 |
| Bis-GMA | 12.00 |
| TMPTMA | 12.00 |
| MEMA | 10.00 |
| TEGDMA | 28.78 |
| CQ | 0.17 |
| ODMAB | 0.50 |
| HMB | 0.50 |
| BHT | 0.05 |

*SM-HEMA is the addition reaction product of styrene-maleic anhydride oligomer and 2-hydroxyethyl methacrylate. The styrene-maleic anhydride oligomer has an average molecular weight of about 1,500.

B) Paste composition (in parts by weight)

| Ingredients | Parts by weight |
|---|---|
| Resin Mixture (A) | 2.60 |
| OX-50[1] | 0.48 |
| TS-530 | 0.10 |
| Calcium FAS filler[2] | 6.82 |

[1]treated with γ-methacryloyloxypropyltrimethoxysilane (A-174).
[2]Calcium Fluoroaluminosilicate filler treated with γ-methacryloyloxypropyltrimethoxysilane (A-174). It has an average particle size of about 1.0 $\mu$m and following composition:

| Ingredients | Parts by weight |
|---|---|
| CaO | 27.0 |
| $Al_2O_3$ | 26.8 |
| $SiO_2$ | 32.6 |
| $P_2O_5$ | 5.6 |
| $F_2$ | 8.0 |

Physical Properties of Paste (B):
Compressive Strength: 365 + 28 MPa

Fluoride Release:

| Time | Cumulative Fluoride release ($\mu$g/$cm^2$) |
|---|---|
| 1 day | 10.9 |
| 1 week | 20.5 |
| 2 weeks | 26.5 |
| 3 weeks | 32.0 |
| 4 weeks | 36.0 |

EXAMPLE 2

A) Resin mixture composition

| Ingredients | Parts by weight |
| --- | --- |
| SM-HEMA* | 36.00 |
| HEMA | 5.00 |
| EOTMPTA | 10.00 |
| TMPTMA | 24.00 |
| TEGDMA | 23.78 |
| CQ | 0.17 |
| ODMAB | 0.50 |
| HMB | 0.50 |
| BHT | 0.05 |

*SM-HEMA is the same as that in Example 1

B) Paste composition (in parts by weight)

| Ingredients | Parts by weight |
| --- | --- |
| Resin Mixture (A) | 2.40 |
| OX-50[1] | 0.48 |
| TS-530 | 0.10 |
| Strontium FAS filler[2] | 6.92 |

[1] treated with γ-methacryloyloxypropyltrimethoxysilane (A-174).
[2] Strontium Fluoroaluminosilicate filler treated with γ-methacryloyloxypropyltrimethoxysilane (A-174). It has an average particle size of about 1.0 μm and following composition:

| Ingredients | Parts by weight |
| --- | --- |
| SrO | 20.1 |
| $Al_2O_3$ | 19.2 |
| $SO_2$ | 30.5 |
| CaO | 8.5 |
| $Na_2O$ | 4.4 |
| $P_2O_5$ | 2.9 |
| $F_2$ | 14.6 |

Physical Properties of Paste (B):
Compressive Strength: 356 ± 37 MPa

Fluoride Release:

| Time | Cumulative Fluoride release ($\mu g/cm^2$) |
| --- | --- |
| 1 day | 6.9 |
| 1 week | 12.0 |
| 2 weeks | 15.6 |
| 3 weeks | 19.1 |
| 4 weeks | 22.3 |

EXAMPLE 3

Resin mixture compositions (in parts by weight)

| Ingredients | A | B |
| --- | --- | --- |
| PMGDM | 15.00 | 30.00 |
| UDMA | 20.00 | 10.00 |
| Bis-GMA | 20.00 | 10.00 |
| TEGDMA | 43.78 | 48.78 |
| CQ | 0.17 | 0.17 |
| ODMAB | 0.50 | 0.50 |
| HMB | 0.50 | 0.50 |
| BHT | 0.05 | 0.05 |

Paste compositions (in parts by weight)

| Ingredients | C | D |
| --- | --- | --- |
| Resin Mixture (A) | 2.40 | — |
| Resin Mixture (B) | — | 2.40 |
| OX-50[1] | 0.52 | 0.53 |
| TS-530 | 0.10 | 0.10 |
| Strontium FAS filler[2] | 7.48 | 7.52 |

[1] treated with γ-methacryloyloxypropyltrimethoxysilane (A-174)
[2] Strontium Fluoroaluminosilicate filler same as that in Example 2

Physical Properties of Pastes C and D:

| | Paste C | Paste D |
| --- | --- | --- |
| Compressive Strength: | 359 ± 17 MPa | 356 ± 15 MPa |

Cumulative Fluoride Release ($pg/cm^2$)

| Time | Paste C | Paste D |
| --- | --- | --- |
| 1 day | 5.3 | 9.4 |
| 1 week | 9.0 | 16.8 |
| 2 weeks | 11.6 | 21.8 |
| 3 weeks | 14.0 | 25.6 |
| 4 weeks | 15.9 | 28.8 |

Other variations or embodiments of this invention will become apparent to one of ordinary skill in the art in view of the above description, and the foregoing embodiments are not to be construed as limiting the scope of this invention.

What is claimed is:

1. A dental composite resin/glass ionomer hybrid restorative composition comprising
   an aromatic-moiety-containing polymerizable resin having at least one ethylenically unsaturated group and at least one carboxylic acid group and selected from the group consisting of:
   the addition reaction product of a styrene-maleic anhydride oligomer and an organic compound having one reactive hydroxyl group and at least one ethylenically unsaturated group,
   a (pyromellitic acid dianhydride)-(glyceroldi(meth)acrylate) adduct (PMGDM), and
   a (pyromellitic acid dianhydride)-(2-hydroxyethyl (meth)acrylate) adduct (PMDM) containing at least 20% of a meta isomer;
   a finely divided ion-leachable fluoroaluminosilicate glass filler, and
   a polymerization initiator system,
wherein said composition is a single-part non-aqueous composition with a compressive strength of at least 250 MPa.

2. The composition of claim 1, wherein said ethylenically unsaturated group is a (meth)acrylate group.

3. The composition of claim 1 wherein said styrene-maleic anhydride oligomer has a weight-average molecular weight in the range of about 300–3,000 and the ethylenically unsaturated group is attached to a styrene-maleic anhydride oligomer backbone through an ester linkage.

4. The composition of claim 3 wherein said styrene-maleic anhydride oligomer has a weight-average molecular weight in the range of about 1,000–3,000.

5. The composition of claim 1 wherein said organic compound is selected from the group consisting of glyceroldi(meth)acrylate and 2-hydroxyethyl (meth)acrylate.

6. The composition of claim 1 wherein said aromatic-moiety-containing polymerizable resin has a concentration in the range of about 0.1% by weight to about 90% by weight.

7. The composition of claim 1 wherein said aromatic-moiety-containing polymerizable resin has a concentration in the range of about 1% by weight to about 60% by weight.

8. The composition of claim 1 wherein said aromatic-moiety-containing polymerizable resin has a concentration in the range of about 3% by weight to about 30% by weight.

9. The composition of claim 1 wherein said filler has a concentration in the range of about 0.5% by weight to about 95% by weight.

10. The composition of claim 1 wherein said filler has a concentration in the range of about 5% by weight to about 90% by weight.

11. The composition of claim 1 wherein said filler has a concentration in the range of about 40% by weight to about 80% by weight.

12. The composition of claim 1 wherein said filler has a mean particle size in the range of about 0.05 μm to about 20 μm.

13. The composition of claim 1 wherein said filler has a mean particle size in the range of about 0.1 μm to about 10 μm.

14. The composition of claim 1 wherein said filler has a mean particle size in the range of about 0.3 μm to about 5 μm.

15. The composition of claim 1 wherein said filler is surface treated with a silane coupling agent.

16. The composition of claim 15 wherein said silane coupling agent is γ-methacryloyloxypropyltrimethoxysilane.

17. The composition of claim 1 further comprising a component selected from the group consisting of
a polymerizable resin having at least one ethylenically unsaturated group,
a colloidal silica,
a non-reactive filler that is substantially non-ion-leachable,
a polymerization inhibitor,
a UV stabilizer, and
combinations thereof.

18. An aromatic-moiety-containing polymerizable resin, for use in a composite resin/glass ionomer hybrid dental restorative composition, said resin having at least one ethylenically unsaturated group and at least one carboxylic acid group and selected from the group consisting of:
the addition reaction product of a styrene-maleic anhydride oligomer and an organic compound having one reactive hydroxyl group and at least one ethylenically unsaturated group,
a (pyromellitic acid dianhydride)-(glyceroldi(meth)acrylate) adduct (PMGDM), and
a (pyromellitic acid dianhydride)-(2-hydroxyethyl (meth)acrylate) adduct (PMDM) containing at least 20% of a meta isomer,
wherein said composition is a single-part non-aqueous composition with a compressive strength of at least 250 MPa.

19. The resin of claim 18 wherein said ethylenically unsaturated group is a (meth)acrylate group.

20. The resin of claim 18 wherein said styrene-maleic anhydride oligomer has a weight-average molecular weight in the range of about 300–3,000 and the ethylenically unsaturated group is attached to a styrene-maleic anhydride backbone through an ester linkage.

21. The resin of claim 20 wherein said styrene-maleic anhydride oligomer has a weight-average molecular weight in the range of about 1,000–3,000.

22. The resin of claim 18 wherein said organic compound is selected from the group consisting of glyceroldi(meth)acrylate and 2-hydroxyethyl (meth)acrylate.

23. A dental composite resin/glass ionomer hybrid restorative composition comprising
an aromatic-moiety-containing polymerizable resin selected from the group consisting of
an addition reaction product of pyromellitic acid dianhydride and 2-hydroxyethyl (meth)acrylate, a meta-isomer of said product comprising at least 20% of said product;
an addition reaction product of pyromellitic acid dianhydride and glyceroldi(meth)acrylate;
an addition reaction product of a styrene-maleic anhydride oligomer and glyceroldi(meth)acrylate, the oligomer having a weight average molecular weight in the range of about 1,000 to about 3,000 and having the (meth)acrylate group attached to a styrene-maleic anhydride oligomer backbone through an ester linkage; and
an addition reaction product of a styrene-maleic anhydride oligomer and 2-hydroxyethyl (meth)acrylate, the oligomer having a weight average molecular weight in the range of about 1,000 to about 3,000 and having the (meth)acrylate group attached to a styrene-maleic anhydride oligomer backbone through an ester linkage,
a finely divided ion-leachable fluoroaluminosilicate glass filler, and
a polymerization initiator systems
wherein said composition is a single-part non-aqueous composition with a compressive strength of at least 250 MPa.

24. The composition of claim 23 further comprising a component selected from the group consisting of
a polymerizable resin having at least one ethylenically unsaturated group;
a colloidal silica,
a non-reactive filler that is substantially non-ion leachable,
a polymerization inhibitor,
a UV stabilizer, and
combinations thereof.

25. An aromatic-moiety-containing polymerizable resin in a composite resin/glass ionomer hybrid dental restorative composition, said resin selected from the group consisting of
an addition reaction product of pyromellitic acid dianhydride and 2-hydroxyethyl (meth)acrylate, a meta-isomer of said product comprising at least 20% of said product;
an addition reaction product of pyromellitic acid dianhydride and glyceroldi(meth)acrylate;
an addition reaction product of a styrene-maleic anhydride oligomer and glyceroldi(meth)acrylate, the oligomer having a weight average molecular weight in the range of about 1,000 to about 3,000 and having the (meth)acrylate group attached to a styrene-maleic anhydride oligomer backbone through an ester linkage; and
an addition reaction product: of a styrene-maleic anhydride oligomer and 2-hydroxyethyl (meth)acrylate, the oligomer having a weight average molecular weight in the range of about 1,000 to about 3,000 and having the (meth)acrylate group attached to a styrene-maleic anhydride oligomer backbone through an ester linkage,
wherein said composition is a single-part non-aqueous composition with a compressive strength of at least 250 MPa.

26. The composition of claim 23 wherein said aromatic-moiety-containing polymerizable resin has a concentration in the range of about 0.1% by weight to about 90% by weight.

27. The composition of claim 23 wherein said aromatic-moiety-containing polymerizable resin has a concentration in the range of about 1% by weight to about 60% by weight.

28. The composition of claim 23 wherein said aromatic-moiety-containing polymerizable resin has a concentration in the range of about 3% by weight to about 30% by weight.

29. The composition of claim 23 wherein said filler has a concentration in the range of about 0.5% by weight to about 95% by weight.

30. The composition of claim 23 wherein said filler has a concentration in the range of about 5% by weight to about 90% by weight.

31. The composition of claim 23 wherein said filler has a concentration in the range of about 40% by weight to about 80% by weight.

32. The composition of claim 23 wherein said filler has a mean particle size in the range of about 0.05 µm to about 20 µm.

33. The composition of claim 23 wherein said filler has a mean particle size in the range of about 0.1 µm to about 10 µm.

34. The composition of claim 23 wherein said filler has a mean particle size in the range of about 0.3 µm to about 5 µm.

35. The composition of claim 23 wherein said filler is surface treated with a silane coupling agent.

36. The composition of claim 35 wherein said silane coupling agent is γ-methacryloyloxypropyltrimethoxysilane.

* * * * *

UNITED STATES PATENT AND TRADEMARK OFFICE
CERTIFICATE OF CORRECTION

PATENT NO. : 5,859,089
DATED : January 12, 1999
INVENTOR(S) : Xuejun Qian

It is certified that error appears in the above-identified patent and that said Letters Patent is hereby corrected as shown below:

Column 8, line 57, "365 + 28 Mpa"   should be -- 365+28MPa --

Column 9, line 33, "$SO_2$"   should be --$SiO_2$--

Signed and Sealed this

Twenty-fourth Day of August, 1999

Attest:

Q. TODD DICKINSON

Attesting Officer  Acting Commissioner of Patents and Trademarks